(12) United States Patent
Makarewicz et al.

(10) Patent No.: US 6,640,117 B2
(45) Date of Patent: Oct. 28, 2003

(54) METHOD AND APPARATUS FOR MINIMIZING SPECTRAL EFFECTS ATTRIBUTABLE TO TISSUE STATE VARIATIONS DURING NIR-BASED NON-INVASIVE BLOOD ANALYTE DETERMINATION

(75) Inventors: Marcy R. Makarewicz, Chandler, AZ (US); Mutua Mattu, Gilbert, AZ (US); Thomas B. Blank, Chandler, AZ (US); Stephen L. Monfre, Gilbert, AZ (US); Timothy L. Ruchti, Gilbert, AZ (US)

(73) Assignee: Sensys Medical, Inc., Chandler, AZ (US)

( * ) Notice: Subject to any disclaimer, the term of this patent is extended or adjusted under 35 U.S.C. 154(b) by 66 days.

(21) Appl. No.: 09/955,531

(22) Filed: Sep. 17, 2001

(65) Prior Publication Data

US 2002/0038080 A1 Mar. 28, 2002

Related U.S. Application Data

(60) Provisional application No. 60/235,369, filed on Sep. 26, 2000.

(51) Int. Cl.⁷ .................................................. A61B 5/00
(52) U.S. Cl. ........................ 600/322; 600/334; 600/474
(58) Field of Search ........................ 600/310, 326, 600/322, 323, 334, 474–477, 549; 356/43; 374/161, 121

(56) References Cited

U.S. PATENT DOCUMENTS

| | | | |
|---|---|---|---|
| 5,007,423 A | * 4/1991 | Branstetter et al. ......... 600/334 |
| 5,615,672 A | 4/1997 | Braig et al. | |
| 5,876,121 A | * 3/1999 | Burns et al. .................. 356/43 |
| 6,002,953 A | 12/1999 | Block | |
| 6,025,597 A | 2/2000 | Sterling et al. | |
| 6,072,180 A | 6/2000 | Kramer et al. | |
| 6,161,028 A | 12/2000 | Braig et al. | |
| 6,241,663 B1 | 6/2001 | Wu et al. | |
| 6,309,884 B1 | 10/2001 | Cooper et al. | |
| 6,466,808 B1 | * 10/2002 | Chin et al. .................. 600/323 |

* cited by examiner

Primary Examiner—Max F. Hindenburg
Assistant Examiner—David McCrosky
(74) Attorney, Agent, or Firm—Glenn Patent Group; Michael A. Glenn; Christopher Feil

(57) ABSTRACT

A method and apparatus for minimizing confounding effects in a noninvasive in-vivo spectral measurement caused by fluctuations in tissue state monitors a selected tissue state parameter spectroscopically and maintains the selected parameter within a target range, at which spectral effects attributable to the changes in the selected parameter are minimized. The invention includes both active and passive control. A preferred embodiment of the invention provides a method and apparatus for minimizing the confounding effects in near IR spectral measurements attributable to shifts in skin temperature at a tissue measurement site. Spectroscopic monitoring of skin temperature at the measurement site provides near-instantaneous temperature readings by eliminating thermal time constants. A thermistor positioned at the measurement site provides active control. The spectrometer and the temperature control device are incorporated into a single instrument for noninvasive measurement of blood glucose concentration.

41 Claims, 10 Drawing Sheets

METHOD AND APPARATUS FOR MINIMIZING SPECTRAL EFFECTS ATTRIBUTABLE TO TISSUE STATE VARIATIONS DURING NIR-BASED NON-INVASIVE BLOOD ANALYTE DETERMINATION

CROSS REFERENCE TO RELATED APPLICATION

This application claims benefit of U.S. Provisional Patent Application No. 60/235,369, filed on Sep. 26, 2000.

BACKGROUND OF THE INVENTION

1. Field of the Invention

The invention relates to the field of noninvasive tissue constituent analysis. More particularly, the invention relates to a method and apparatus for minimizing spectral effects in NIR spectral measurements for noninvasive blood analyte determination attributable to tissue state variations.

2. Description of Related Art

Near infrared (NIR) tissue spectroscopy is a promising noninvasive technology that bases measurements on the irradiation of a tissue site with NIR energy in the 700–2500 nanometer wavelength range. The energy is focused onto an area of the skin and propagates according to the scattering and absorption properties of the skin tissue. Therefore, the reflected or transmitted energy that escapes and is detected provides information about the tissue volume that is encountered. Specifically, the attenuation of the light energy at each wavelength is a function of the structural properties and chemical composition of the tissue. Tissue layers, each containing a unique heterogeneous particulate distribution, affect light absorbance through scattering. Chemical components such as water, protein, fat and blood analytes absorb light proportionally to their concentration through unique absorption profiles or signatures. The measurement of tissue properties, characteristics or composition is based on detecting the magnitude of light attenuation resulting from its respective scattering and/or absorption properties.

While noninvasive prediction of blood analytes, such as blood glucose concentration, has been pursued through NIR spectroscopy, fluctuations in tissue state, such as skin temperature, lead to increased spectral variance that can lead to a reduction of the net analyte signal, thus rendering it difficult to extract valuable analyte information.

Human tissue can consist of as much as 80% water, which has a known peak shift that is a function of temperature, in the NIR absorbance spectrum. As temperature increases, the water band shifts to shorter wavelengths as a result of a decrease in hydrogen bonding. As light irradiates the tissue and travels through the layers of the skin, it is scattered and absorbed by the constituents of the skin before exiting the skin, where it is detected by a spectrometer. Skin temperature variation is introduced into the spectral measurement in two ways. First, the resulting signal contains spectral information from the tissue volume it has traversed, including contributions from the natural temperature gradients present in the optical sampling path of human tissue. Second, human skin and sub dermal tissue undergo temperature variations, as a result of environmental and physiological factors, to maintain a uniform core body temperature. During the course of a day, skin temperatures have been observed to fluctuate by as much as 5° F. in healthy individuals. These factors result in temperature variations between the measurements comprising a data set. Therefore, water band shifts within a measurement and between measurements are present in the data set. The data set is used to estimate the analyte of interest through the development of a multivariate mathematical calibration model.

Within and between measurement temperature variations add a level of complexity to the multivariate analysis, making it more difficult to extract valuable analyte information. Large variations in temperature lead to increased spectral variance that can lead to a reduction of the net analyte signal. In addition, uncontrolled skin temperature variations have a higher probability of correlating with analytes of interest. Such chance correlations can lead to false calibrations, which may or may not be discernible.

Various spectroscopic methods and apparatuses that aim to monitor or alter sample temperature in some way are described in the prior art. For example, J. Braig, D. Goldberger, B. Sterling, *Self-emission noninvasive infrared spectrophotometer with body temperature compensation*, U.S. Pat. No. 5,615,672 (Apr. 1, 1997) describe a "self-emission" glucose monitor that noninvasively measures glucose concentration in a subject's blood by monitoring the infrared emission of glucose in the blood at long infrared wavelengths near 10 microns. The described device utilizes the infrared energy emitted by the person's blood and/or surrounding tissue to perform the absorption analysis. A temperature-sensing device for measuring the person's internal temperature at the arm is also used to adjust the constituent concentration measurement for temperature dependent effects. While the use of the person's own infrared energy, emitted as body heat, for an infrared source eliminates the necessity of providing an energy source, the described device and the attendant method require a determination of the individual's internal temperature; however, the sensor measures temperature at the skin surface. Therefore, the calculated compensation for internal body temperature to be applied to the measured spectral signal introduces a significant source of error in the analyte concentration estimate. Additionally, the sensor's thermal time constant introduces an undesirable latency into the measurement, possibly as long as 1½ minutes. Furthermore, the described device merely calculates a correction to be made to the spectral signal that compensates for the effect of the subject's body temperature. No provision is made for control of temperature within a target range in order to provide an optimal sample temperature, at which temperature-related spectral effects are minimized. Additionally, the Braig, et al. teachings are concerned with the mid- and far regions of the IR spectrum.

M. Block, *Non-invasive IR transmission measurement of analyte in the tympanic membrane*, U.S. Pat. No. 6,002,953 (Dec. 14, 1999) describes non-invasive methods and apparatuses for measurement of concentrations of selected blood constituent in which an optical device is inserted into the external ear canal to direct a portion of the electromagnetic radiation onto an IR detection and analysis device. The tympanic membrane is cooled to create a temperature differential with the inner ear, thus facilitating the emission of thermal radiation across the tympanic membrane. The insertion of an optical instrument deep into the ear canal and chilling of the tympanic membrane are by no means invasive, although they may be seen to be minimally invasive compared to more traumatic methods of sampling, such as venipuncture. The Block teachings make no provision for spectroscopy-based measurement of temperature at the measurement site. The cooling of the tympanic membrane is not done to minimize spectral effects of tissue state fluctuation, but to facilitate thermal transfer. With the exception of cooling the tympanic membrane in a stereotypical fashion, the Block device is incapable of controlling temperature at the measurement site. The Block device further provides no closed loop in which spectroscopic temperature determinations provide the feedback required for control of site temperature.

J. Braig, C. Kramer, B. Sterling, D. Goldberger, P. Zheng, A. Shulenberger, R. Trebino, R. King, C. Barnes, *Method for determining analyte concentration using periodic temperature modulation and phase detection*, U.S. Pat. No. 6,161,028 (Dec. 12, 2000) describe a method of determining the analyte concentration of a test sample that employs a rationale similar to that of Block. A temperature gradient is introduced in the test sample and infrared radiation detectors measure radiation at selected analyte absorbance peak and reference wavelengths. The Braig, et al. teachings employ gradient spectroscopy, in which a temperature gradient is produced in the sample to facilitate thermal transfer, thereby delivering more thermal radiation to the radiation detectors. The method described does not address the problem of spectral effects related to fluctuations in tissue state at the measurement site and their confounding effect on the net analyte signal. With the exception of inducing a temperature gradient in the sample, the described method provides no way of controlling sample temperature within a target range that minimizes the spectral effects caused by fluctuations in sample temperature.

In view of the problems left unsolved by the prior art, there exists a need for a way to control spectral effects attributable to tissue state variations, such as skin temperature, during NIR-based, non-invasive blood analyte determination, by monitoring the selected tissue state parameter and maintaining it within a predetermined target range of values at which such spectral effects are minimized. It would be a significant technological advance to monitor the tissue state parameter spectroscopically, in which a calibration model calculates measured values by correlating shifts in the selected tissue state parameter with shifts in observed spectral effects, thus eliminating the time constants imposed by conventional sensor devices. It would be desirable to provide a means of controlling the selected tissue state parameter, driven by a closed loop, in which the calculated values provided the feedback for determining the degree of control to be applied.

SUMMARY OF THE INVENTION

The invention provides a method and apparatus for minimizing confounding effects in a noninvasive in-vivo spectral measurement caused by fluctuations in tissue state. A selected tissue state parameter is spectroscopically monitored through the application of a multivariate calibration model that correlates spectroscopic changes with fluctuations in the selected tissue state parameter, providing near-instantaneous measurements, without the imposition of any significant time constants. A target range of values for the selected parameter is empirically determined from an experimental data set by observing the spectra of the data set to determine a range of values at which spectral effects due to attributable to the changes in the selected parameter are minimized. During measurement, the selected parameter is continuously monitored. The calculated values provide feedback in a closed loop that drives a device for maintaining the selected tissue state parameter within the target range. Means for both active and passive control of the tissue state parameter are included in the invention.

A preferred embodiment of the invention provides a method and apparatus for minimizing the confounding effects in a noninvasive near IR spectral measurement attributable to shifts in skin temperature at the tissue measurement site. Skin temperature at the measurement site is spectroscopically monitored by calculating temperature values through the application of a multivariate calibration model that correlates spectroscopic changes with shifts in skin temperature. Thermal time constants imposed by conventional temperature sensing devices are eliminated, providing near-instantaneous temperature readings. Active and passive control means are provided. Passive control is achieved through the selective application and removal of an occlusive thermal wrap. Active control is provided by a thermistor applied to the skin in the vicinity of the measurement site. Active and passive control may be applied in complementary fashion or they may be used separately. In a particularly preferred embodiment of the invention, the control means is incorporated into the measurement instrument, wherein the calculated skin temperature values provide the feedback in a closed loop that drives the control device. In an alternate embodiment of the invention, the temperature values are supplied to an operator, who then applies active and/or passive control to achieve and maintain a skin temperature within the target range. By monitoring skin temperature spectroscopically and employing methods of passive and/or active control it is possible to reduce the effects of skin temperature variation on the NIR measurement. The invention finds particular application in the non-invasive measurement of blood glucose concentration.

BRIEF DESCRIPTION OF THE DRAWINGS

FIGS. 9a through 11a provide plots of spectral variance versus wavelength for three healthy subjects, according to the invention;

FIGS. 9b through 11b provide plots of minimized and large temperature variation for the three subjects of FIGS. 9a–11a, according to the invention;

Figure 1:
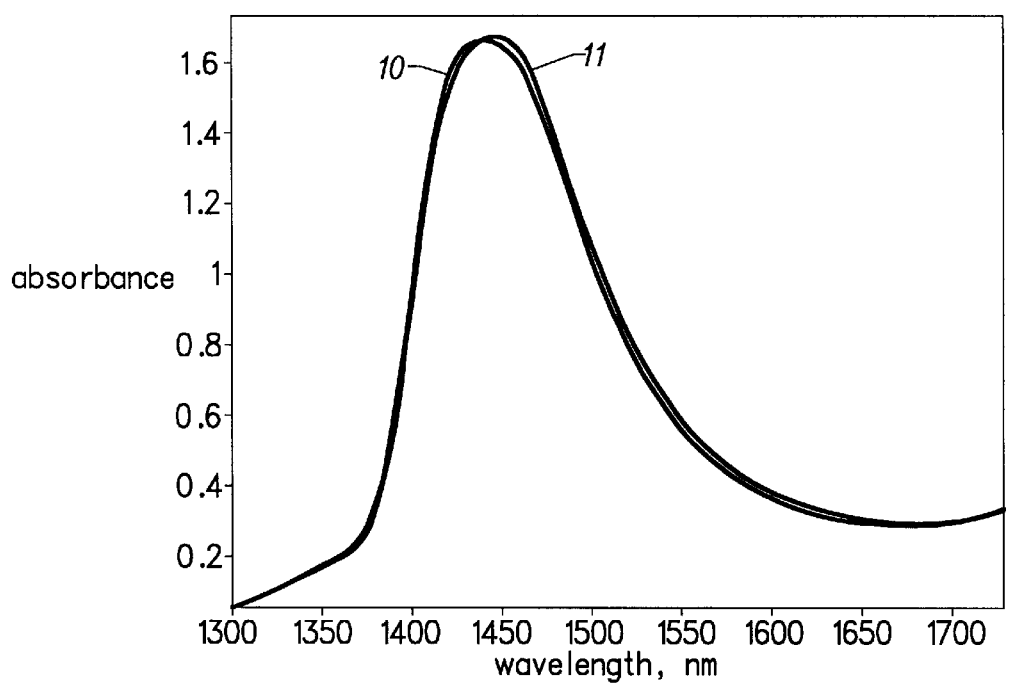
FIG. 1 provides absorbance spectra, showing a water absorbance peak, measured at two different temperatures.

DETAILED DESCRIPTION
Skin Temperature Measurement and Control Using NIR Spectroscopy Near Infrared measurements of skin combined with associated skin temperature reference measurements are used to develop NIR temperature calibrations that require only NIR tissue scans to predict skin surface temperature. Methods of developing calibrations for spectral analysis may employ a variety of multivariate analytical techniques that are well known to those skilled in the art. NIR skin temperature calibration is made possible by the known shifting of the 1450 nm water band with variations in skin temperature. The calibration model incorporates the shift information implicitly in the multivariate regression coefficients. Temperature measurement and control of human tissue is important in noninvasive NIR measurement because it provides a means of simplifying the complex overlapping spectral effects that inhibit extraction of the analyte signal. The extra temperature measurement hardware and the associated cost and complexity are avoided by using NIR temperature measurement.

An advantage of the NIR measurement over the primary thermistor measurement lies in the absence of thermal time constant inherent in conventional sensing hardware. Measured skin thermistor response frequently requires as much as 1½ minutes to reflect 95% of the sample temperature change under a step change of 10° F. Eliminating the time constant in the temperature measurement provides significant advantages in the implementation of active closed-loop temperature control of the skin by providing near-immediate skin temperature feedback unimpeded by the time constant inherent in primary measurement methods.

Skin temperature calibrations for multiple individuals have been established using the calibration data from a single subject. This result foretells the feasibility of general skin temperature calibrations that can be established on site prior to the shipment of the instrument.

Procedures for active and passive control of skin temperature are provided below. Near infrared (NIR) tissue spectroscopy is utilized to irradiate the skin and estimate biological analytes of human subjects. Skin temperature variation is destructive to the NIR measurement in two ways: First, false calibrations can occur if skin temperature correlates to analytes of interest, and second, large skin temperature fluctuations decrease the net analyte signal. An apparatus and procedure to passively and actively control skin temperature to prevent decreasing the net analyte signal and spurious correlations is described. The procedure for controlling skin temperature involves determining the target skin temperature, monitoring the actual skin temperature, and applying passive and/or active control methods to attain the target temperature.

Experiments were conducted to:
Characterize the effects of skin temperature variation on the NIR spectrum—see Experiments I and II, below.
Characterize skin temperature profiles over the course of a day and between days, and to determine target temperatures—see Experiment II and III, below.
Test methods of controlling skin temperature to within ±1° F.—see Experiment III, below.

Methods of Skin Temperature Control

One of the primary functions of the skin is to maintain a constant body temperature. Physiological responses to external and internal stimuli can limit skin temperature control. Periodic monitoring is a critical step in achieving good temperature control. Using the invention, the skilled practitioner is enabled to discern trends in skin temperature and implement passive and/or active control as compensation, thus maintaining a stabilized skin temperature at the spectral measurement site.

Skin temperature is monitored using a temperature probe attached to the skin within 5 mm of the spectral measurement site. As the discussion of Experiment II, below shows, daily skin temperature profiles have shown that temperatures are generally lower in the morning and gradually increase throughout the day, resulting in a profile with a gentle positive slope that stabilizes with time. As indicated in the discussion of Experiment III, below, healthy and diabetic skin temperature profiles have resulted in an initial target skin temperature range of 90–92° F., representative of temperatures observed in the mid- to late afternoon. Target ranges may vary depending on the individual. The following methods are utilized to achieve and maintain the target range:

Passive Control

Passive control, by means of a thermal wrap placed around the subject's forearm, can be implemented to quickly drive the skin temperature to the target temperature in the morning. This results in a profile with a steep positive slope during the first hour, followed by more uniform skin temperatures during the rest of the day. The wrap covers the forearm from the wrist to elbow and, therefore raises the temperature of the entire forearm. The wrap can be adjusted loosely or snuggly around the subjects arm, or removed, as needed to maintain the skin temperature within the target range.

Active Control

Active control utilizes a temperature-controlled copper heat sink to rapidly change the temperature of the skin. The set point of the heat sink can be adjusted to warm or cool the skin. Active control is localized to the skin that comes into contact with the heat sink, which has the same dimensions as the subject-spectrometer interface. If the skin temperature is significantly outside of the target range just prior to the spectral measurement, the arm is placed on the heat sink for 1–2 minutes before the measurement.

Figure 14:
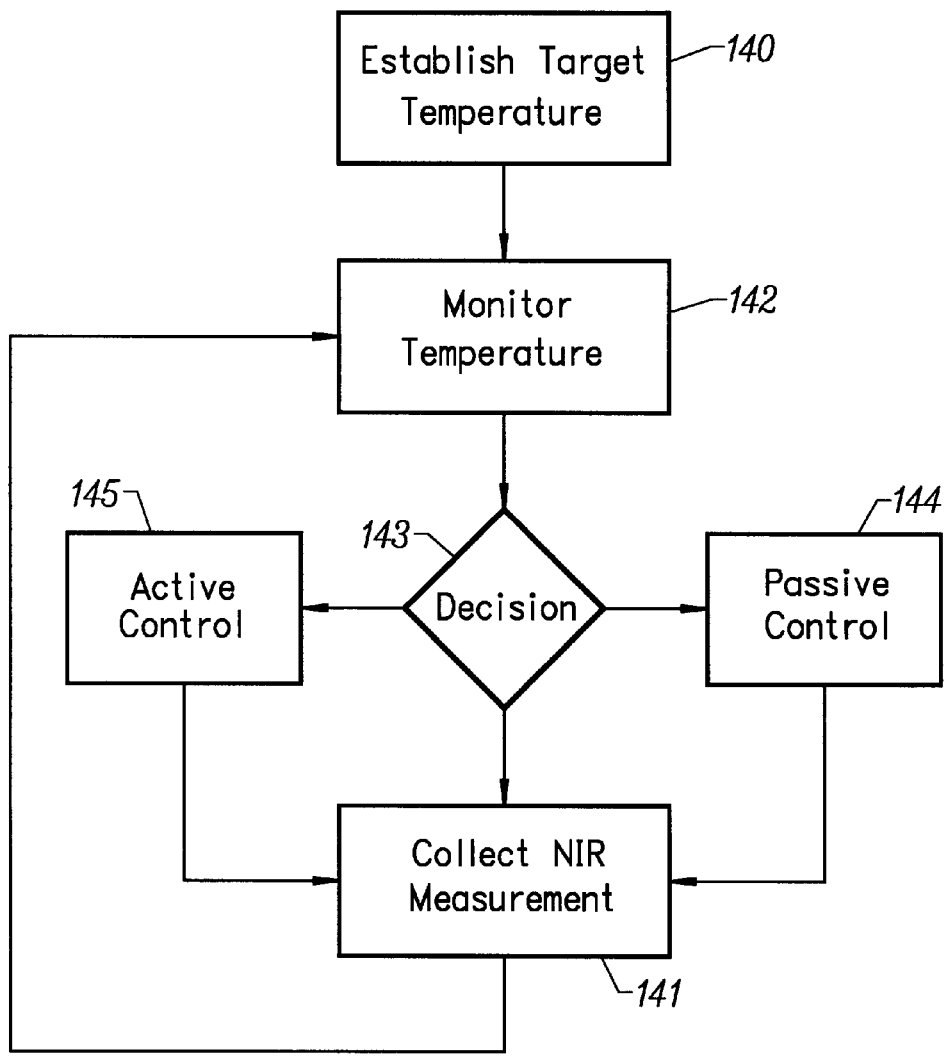
FIG. 14 provides a block diagram of a method for measuring and controlling skin temperature at a tissue measurement site, according to the invention.

The methods presented above can be used in a complementary fashion to maintain skin temperature within the target range. The method chosen is a function of the time available before the spectral measurement and observed skin temperature. The decision to implement active or passive control is made each time the skin temperature is monitored based upon the time available before the spectral measurement and the difference between the actual and target temperatures. Passive control is best suited for time periods greater than 1–2 minutes, whereas active control is advantageous if rapid temperature increases or decreases are required. A flow diagram of a general procedure to control skin temperature is presented in FIG. 14. As described herein, a target temperature is established 140 empirically by observing spectral measurements and establishing a target range at which spectral variation is kept to a minimum. NIR spectral measurements are collected 141, and skin temperature is monitored 142 spectroscopically by the application of a multivariate calibration to the spectral measurement that correlates spectral effects with skin temperature. The temperature reading is evaluated 143. If skin temperature is within the target range, no control is implemented. If the skin temperature is outside of the target range, either passive 144 or active 145 control, or a combination of both, are implemented to bring temperature back into the target range. It can be seen from FIGS. 14 and 15 that the system of the current invention represents a closed loop, in which the control devices are driven by the feedback supplied by the spectroscopic temperature determinations.

Figure 15:
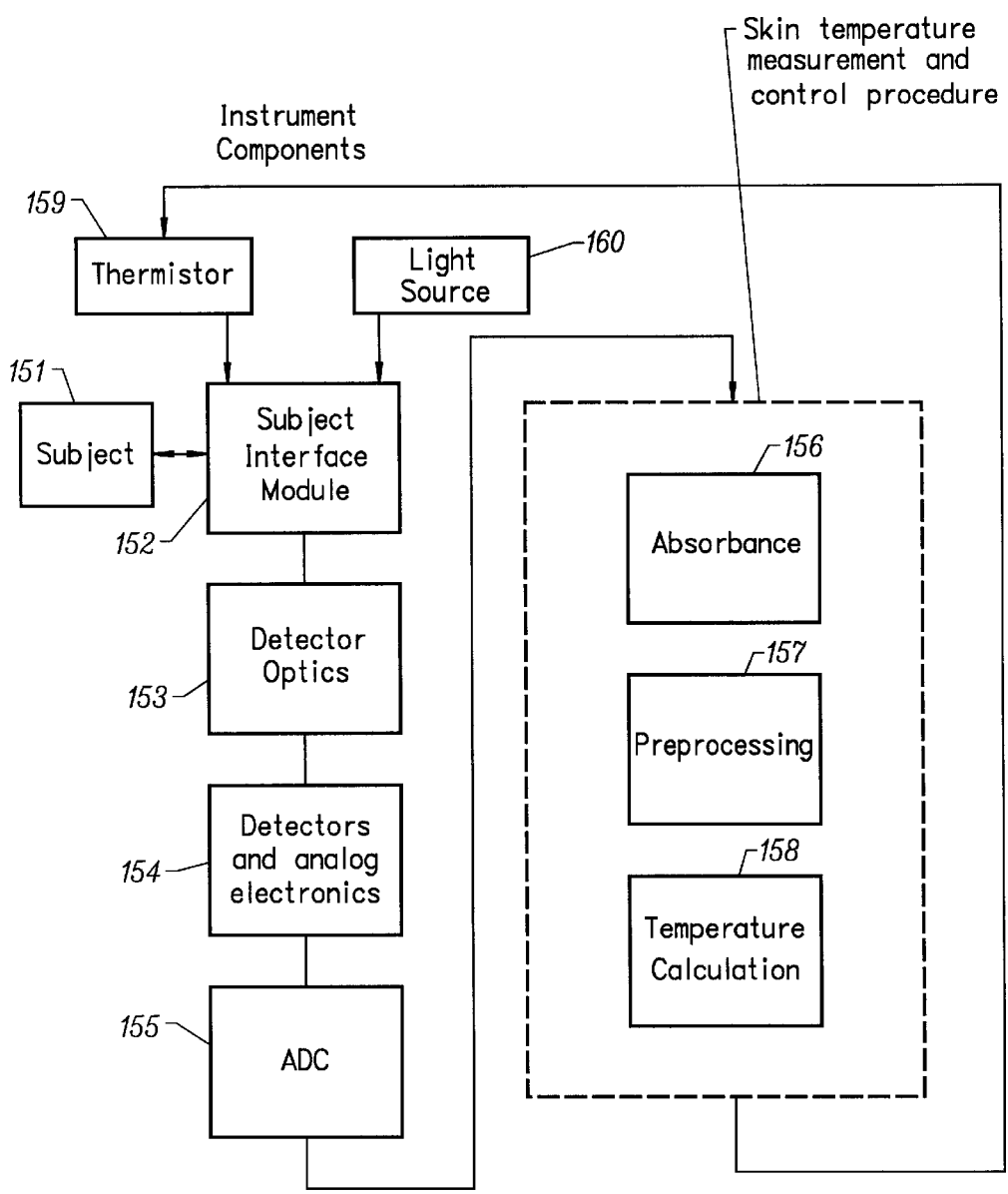
FIG. 15 provides a block diagram of a spectrometer instrument for measuring and controlling skin temperature at a tissue measurement site, according to the invention.

A spectrometer instrument for implementing the invented method is shown in FIG. 15. A subject interface module 152 is coupled with a tissue measurement site on the skin of the subject 151. A thermistor 159 mounted within the subject interface module has a set point within the target range. In order to maintain its set point, the thermistor either heats or cools the skin surface. In a preferred embodiment of the invention, the subject interface module comprises a fiber optic probe. The subject interface module directs light emitted from the light source 160 toward the tissue measurement site. Light that is back diffused form the tissue measurement site is directed toward one or more photo detectors 154 by detector optics 153, in this case, a fiber optic. Analog electronics convert the detected light to a voltage, which is subsequently converted to a digital value by an analog-to-digital converter (ADC) 155. From these digital values, an absorbance spectrum is calculated 156. The absorbance spectrum may be subjected to one or more of the preprocessing techniques 157 previously described. Subsequently, a temperature value is calculated 158 from the absorbance spectrum through the application of the calibration model previously described. Finally, the calculated temperature value is routed to a controller (not shown) that interfaces with the thermistor 159, to provide temperature feedback.

Experiment I: Impact of Skin Temperature on NIR Spectra

Summary

A preliminary study was conducted in order to determine if the optical configuration of the FOCSI (fiber optic coupled scanning instrument) spectrometer instrument, supplied by Instrumentation Metrics, Inc., Tempe Ariz., was superior to the optical configuration of the DRACO spectrometer instrument, also supplied by Instrumentation Metrics, Inc. with respect to the information content contained in the water band of the NIR spectrum. The water band at 1450 nm is known to shift with sample temperature, rendering the modeling of glucose in water and tissue more difficult over samples that are taken at widely varying temperatures. Therefore, a blood glucose prediction algorithm must incorporate a calibration strategy that utilizes the shift in the water band to simplify the modeling challenges. Thus, an optical design that permits evaluation of tissue temperature information is an important design criterion for a noninvasive glucose monitor. In this study, it was observed that noninvasive measurements taken at different temperatures on the FOCSI instrument were substantially more consistent with the expected spectral behavior than those taken on the DRACO. It is suspected that the highly variable sample pathlength inherent in the noninvasive DRACO measurement confounds the interpretation of temperature effects.

Introduction

Water, comprising as much as 80% of human tissue, has a known peak shift in the NIR absorbance spectrum with increasing sample temperature. The shift of the water band to shorter wavelength arises as a result of the increased solution pH and a concomitant decrease in hydrogen bonding with increasing temperature. In FIG. 1, the transmission spectrum of the first-overtone band of water is plotted at 33 (11) and 41 (10) degrees centigrade. An in vivo measurement peak can be expected to contain spectral contributions from a distribution of temperature states due to a natural temperature gradient present in the optical sampling path of human tissue. Modeling glucose in this thermally complex sample matrix is one of the more significant challenges of in vivo measurement using NIR spectroscopy. Accurate compensation for tissue temperature is best approached by inference from the spectral measurement because probing tissue with near infrared light is likely to lead to localized effects on the surface and in the tissue. A temperature probe cannot be inserted into the light path of the spectrometer without disturbing the measurement and a non-invasive temperature probe will not account for temperature gradients in tissue. The most effective means of compensating for tissue temperature variation requires that the measured spectrum contain substantive information about the position and shape of the water band. The shape of the water band is also influenced by tissue optics, making the acquisition of highly informative spectral scans even more important. In light of these considerations, instrumental or sampling artifacts that distort the shape of the water band are highly undesirable and should strongly influence the design of non-invasive glucose instrumentation based on NIR spectroscopy.

Experimental

Six subjects were scanned on both the FOCSI and DRACO scanning spectrometers. Two sets of experiments were conducted on each subject. In the first experiment, the subject was scanned at normal ambient skin temperature, while the second experiment was conducted after preheating subjects' skin temperature to 3–5° F. above the normal skin temperature. Measurements taken prior to the study led to the establishment of the following protocols for spectrum measurement: Rapid temperature and physiological changes were reduced by allowing 3 minutes of arm contact with the instrument subject interface module prior to the acquisition of spectra. A YSI 4000 skin temperature sensor, supplied by YSI, Inc., Yellow Springs Ohio, with a readout to ±0.05° F. was placed about 5 mm from the measurement site during the course of the experiments. Temperature was recorded every 30 seconds and scans were conducted over a period of two minutes. Reference spectra using an 80% reflectance standard were acquired directly before and after the in vivo measurement.

Results and Discussion

Figure 2:
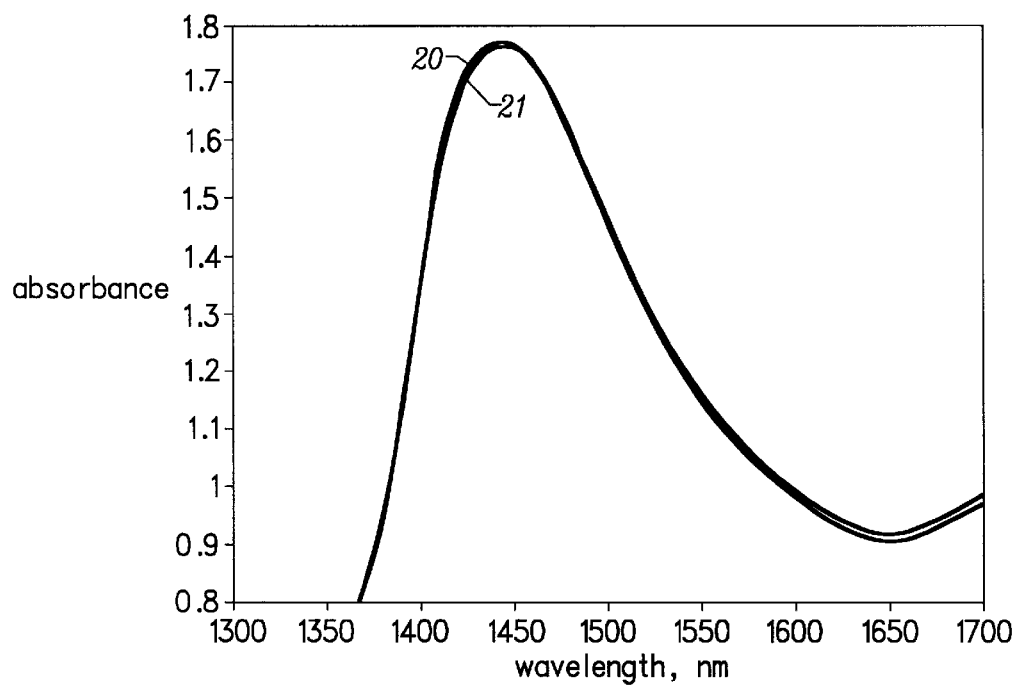
FIGS. 2 and 3 provide absorbance spectra, showing a water absorbance peak, of two different subjects measured on a spectrometer instrument having a fiber optic subject interface, according to the invention.
Figure 3:
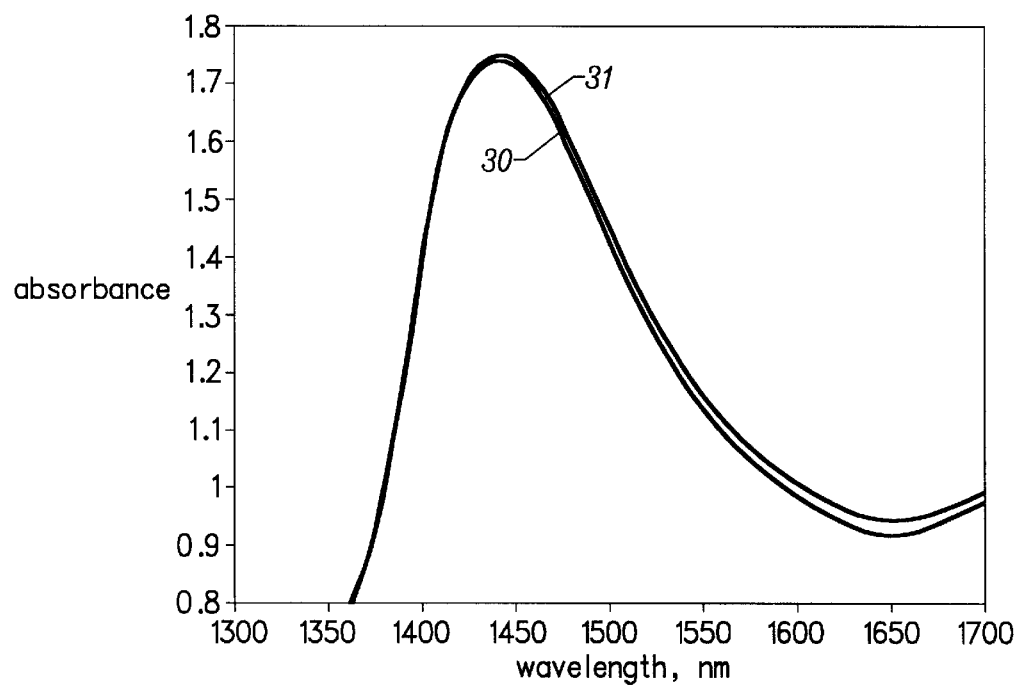

Scans taken on each spectrometer instrument were examined for temperature related effects for each of the six subjects. Temperature related effects that are consistent with a change in the temperature distribution of sample tissue were noted in three of the four remaining patients scanned on the FOCSI, but temperature related effects were not as obvious in the scans taken on the DRACO. In FIGS. 2 and 3, the scans taken on the FOCSI from two individuals at two temperature levels are plotted. One set of spectra were taken at skin temperatures 5° F. (21, 30) higher than the other (21, 31). It is evident that the higher temperature scans had greater difference in intensity between the 1450 nm maximum and the minimum absorbance at 1650–1700 nm. The edge of the high temperature spectrum peak is also on the inside of the low temperature spectrum on the long wavelength side of the 1450 nm water band. These spectral differences are consistent with the existence of a more narrow range of water temperatures in the heated tissue, giving rise to a sharper peak. According to scattering theory, the scattering of tissue increases with temperature. The spectral region with the most dominant scattering effects is in the short wavelength region around the second-overtone band at 1100–1300 nm. Scattering is believed to diminish rapidly after the second overtone region. Suppression in the sample absorbance with increasing temperature is consistent with the expected optical behavior of tissue. The absorbance decrease from increased scattering with temperature is pronounced at the second overtone, but it may also be significant at the first overtone on highly absorbed spectral features like the maximum of the water band.

Figure 4:
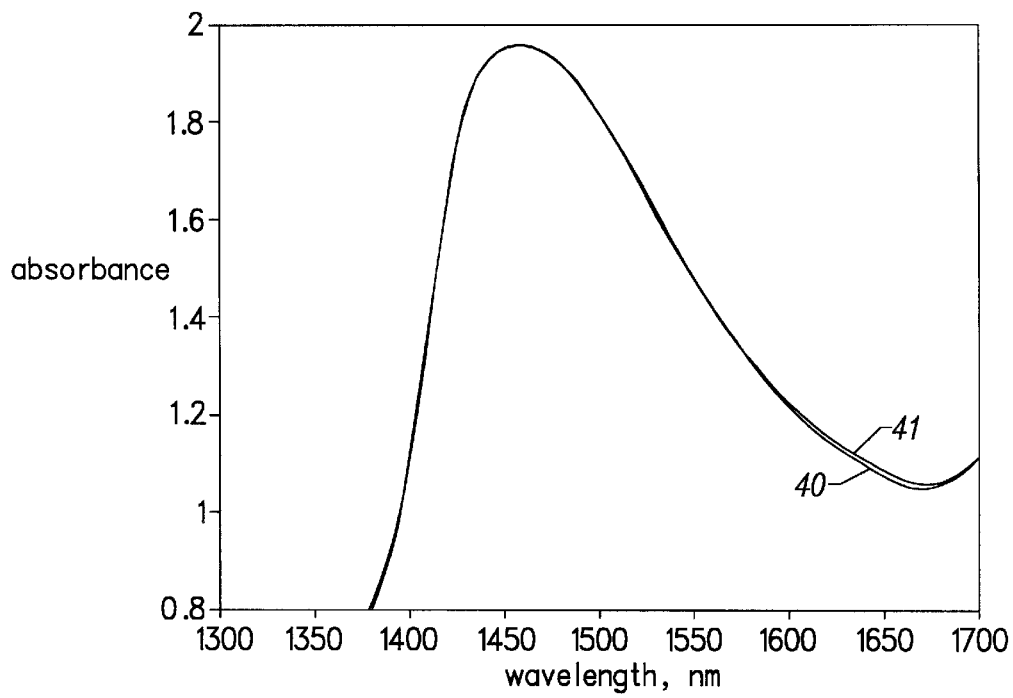
FIGS. 4 and 5 provide absorbance spectra of the subjects of FIGS. 2 and 3, measured on a spectrometer instrument having a subject interface constructed from lenses, according to the invention.
Figure 5:
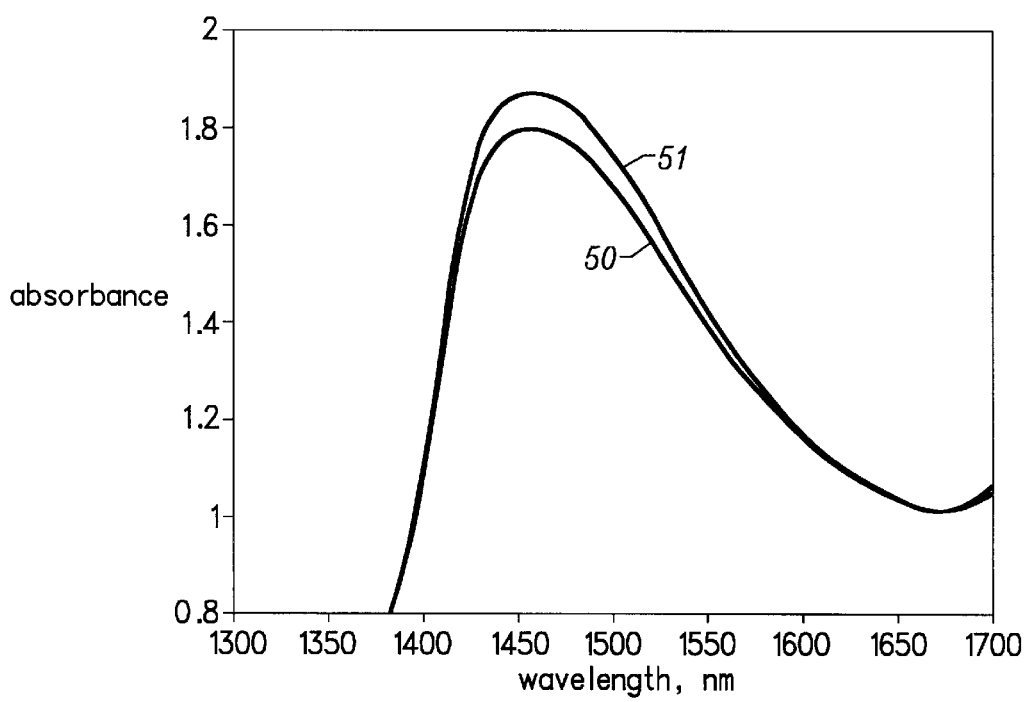
Figure 6:
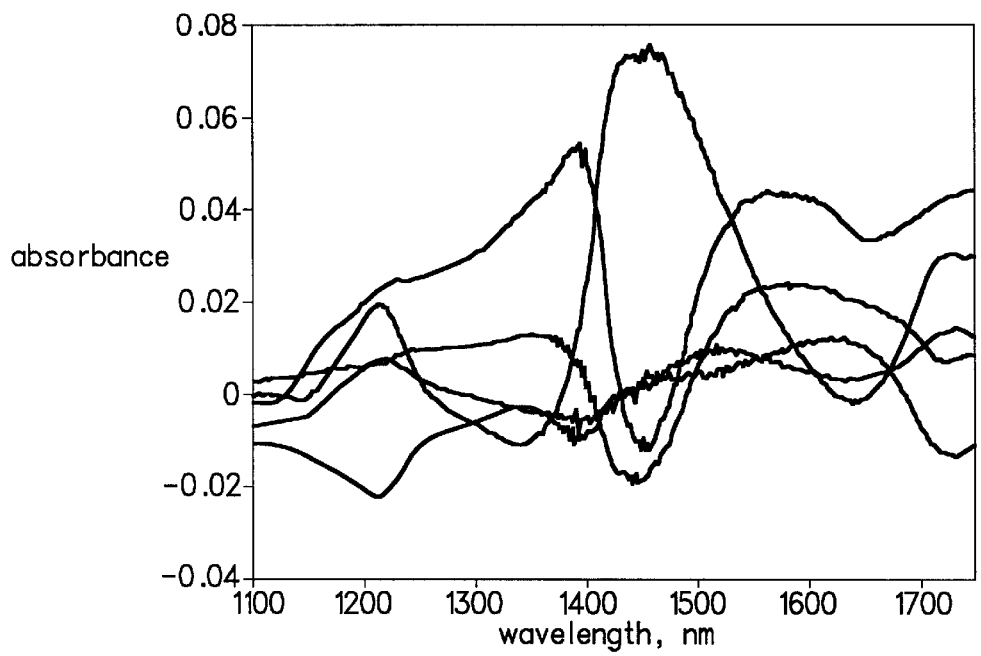
FIG. 6 shows difference spectra for the absorbance spectra of FIGS. 2 and 3, according to the invention.
Figure 7:
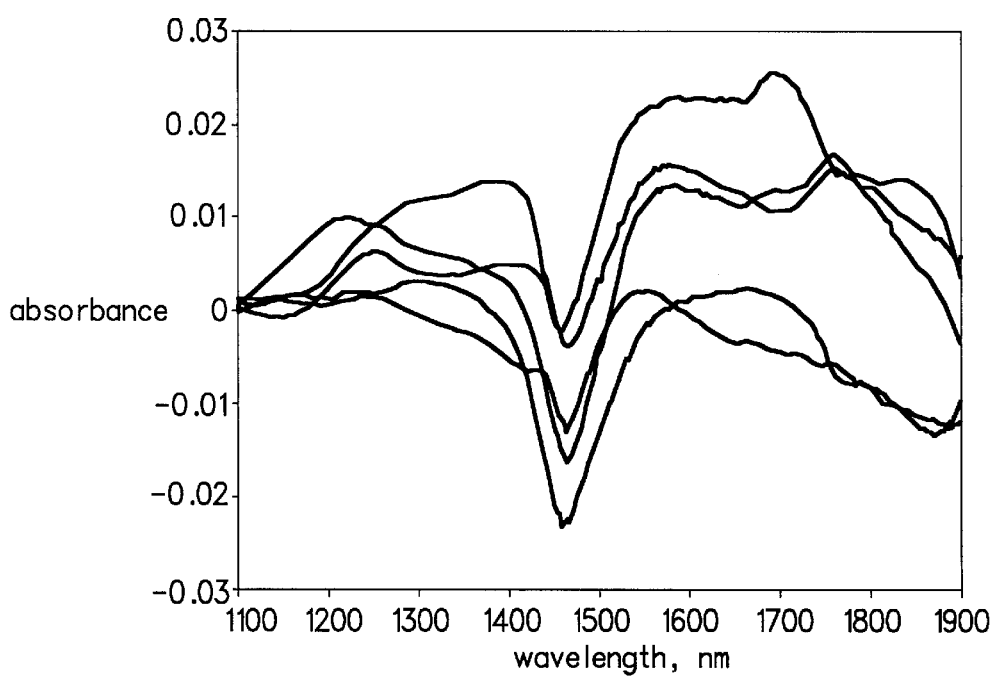
FIG. 7 shows difference spectra for the absorbance spectra of FIGS. 4 and 5, according to the invention.

The corresponding scans 40, 50 and 41, 51 taken on the DRACO are plotted in FIGS. 4 and 5. As previously mentioned, temperature effects are not nearly as noticeable as they are in the spectra of FIGS. 2 and 3. Difference spectra calculated using the individual subject spectra taken at cool and warm skin temperatures should contain spectral information related to temperature changes in the tissue. A consistent measurement should yield difference spectra of similar shape for each of the individual test subjects. The spectra acquired for each subject at cool and warm skin temperature were subtracted and the resulting difference spectra for the DRACO spectrometer are plotted in FIG. 6 and those for the FOCSI instrument are plotted in FIG. 7. Clearly the difference spectra (Cold minus hot) are more consistent in shape for the FOCSI experiments than for the measurements taken with the DRACO. The temperature-induced scattering effects around the second-overtone region are consistent with scattering research for the FOCSI in that the cold minus the hot spectrum consistently yielded the positive residual expected from increased scattering by tissue at elevated temperature. It is obvious from FIGS. 6 and 7 that interpretations of measurements on tissue at normal and warmed temperature states using the DRACO optical system were not as simple as the corresponding measurements taken on the FOCSI. The DRACO optical system may be more susceptible to variations in tissue sampling and surface reflection that may arise due to sensor positioning and pressure.

Conclusions

The temperature studies conducted here can be used to confirm that the FOCSI subject interface module was more effective than the DRACO subject interface module for collection and identification of temperature-related variation present in in vivo spectral measurements. Differences in the spectra of normal and heated tissue were on the order of several hundredths of an absorbance unit, making the noise disadvantage of the DRACO detectors a non-issue in these comparisons. The greatest remaining difference between the units was in the optical sampling systems: The DRACO with a conventional lens system and the FOCSI with a fiber optic light transport system running from the monochromator to the sample and back to the detectors. The presence of a significant level of variable skin surface reflectance and a wider optical path distribution inherent to the DRACO measurements was expected to lead to broadening and shape uncertainty in the water band at 1450 nm. See J. D. Hardy, H. T. Hammel, D. Murgatroyd, *J Appl. Physiol.*, 9:257 (1956). Alternately, the FOCSI system was expected to have a negligible surface reflectance component and a more narrow distribution of sample pathlengths for photons that reach the instrument detectors. These optical differences between the DRACO and the FOCSI were expected to contribute to lower information content in the water band measured by the DRACO. Additionally, other, less obvious factors would significantly limit or enhance the interpretation of temperature related spectral variation.

It was encouraging that temperature related spectral variation of scans taken on the FOCSI was consistent with the expected spectral shift and optical scattering properties of water and human tissue. Significantly, experiments on the DRACO were not as successful at producing systematic spectral variation with skin temperature. The most likely source of the measurement inconsistency of scans taken on the DRACO is the sample-to-sample variation in skin surface reflectance. Unfortunately, even modest changes in surface reflectance between different measurements of the same subject can lead to changes in the amplitude and shape of the water band, which in turn make the interpretation of temperature-related spectral variation difficult or impossible. In vivo sample scattering and the related changes in mean optical path can vary with changes in temperature, pressure, physiological response, and sampling location. Compensation for temperature requires that temperature-related variation could be largely separated from these other effects. Resolution of skin temperature states is made substantially more challenging on the DRACO instrument because the spectral variation due to factors other than temperature is larger than for the FOCSI instrument. The consistency of the measurements taken in this experiment and the resulting information content lead to the conclusion that a fiber-based instrument is preferred for use in compensation of temperature-related spectral variation.

Experiment II: Skin Temperature Profiles

Summary

The objective of the current study was to characterize skin temperature profiles, both uncontrolled and with passive skin temperature control. Both uncontrolled and passively controlled skin temperatures were found to be lowest early in the day, with a tendency to stabilize as the day progressed. The passively controlled and the uncontrolled profiles tended to track each other, although passively controlled skin temperature were less susceptible to sudden changes.

Experimental

Eight subjects were divided into two groups, each group including three males and one female. Both uncontrolled and passively controlled skin temperature profiles were collected on an hourly basis between 9 AM and 6 PM for three days. For group one, skin temperature was passively controlled by occluding a measurement site on the forearm with a THERMAX wrap. For group two, passive control was by means of the THERMAX wrap on day one. On days two and three, control was by means of a fleece arm sleeve that covered the entire forearm. For both groups, the uncontrolled temperature measurements were collected on the subjects' other forearms, which were left unoccluded. Skin temperature determinations were made using a YSI 4000 temperature sensor.

Results and Discussion

It was observed that initial temperature was dependent on subjects' clothing: subjects wearing long sleeves had higher initial temperatures. All eight subjects were right-handed, and it was observed that right arm temperatures were generally higher. Subjects' arm temperatures did not necessarily correlate with room temperature; typically arm temperature rose steeply in the morning, then it either stabilized and eventually dropped, or continued to rise in a more gradual fashion than the initial steep rise. The day-to-day highest temperature in the passive controls occurred in a relatively narrow range of 91–93° F. for seven of the eight subjects. Day-to-day lowest temperature was highly variable and may have been affected by ingestion of stimulant beverages such as coffee and soft drinks. Passively controlled skin temperatures were generally less susceptible to sudden changes in temperature of the external environment, such as when the subject went outside. After the initial AM rapid temperature increase, the controlled and the uncontrolled profiles tended to track each other, with the spread between uncontrolled and controlled temperatures remaining fairly constant. This may have been a result of a sympathetic response that tended to stabilize temperatures between the uncontrolled arm and the controlled arm. Finally, it was observed that skin temperature could by increased approximately 2–9° F. by covering the entire forearm with the fleece arm sleeve.

Conclusions

Skin temperature is subject to a number of environmental and physiologic influences. The use of various passive control strategies can minimize skin temperature fluctuations to such a degree that a range of ±1° F. may be maintained. Application of passive temperature controls can precipitate rapid increases in skin temperatures.

Experiment III: Preliminary Effects of Skin Temperature on Sample Repeatability

Summary

The current studies focus on the relationship between skin temperatures and noninvasive spectra, in particular, how large skin temperature excursions impact sampling precision. A study was conducted in which noninvasive spectra were collected over a large range of skin temperatures as well as over a controlled range of skin temperatures for each of three subjects. Preliminary results indicate that minimal skin temperature variation leads to a reduction of the spectral variance in the 1500–1600 nm wavelength region.

Introduction

Skin temperature data from a first pool of diabetic test subjects undergoing repeated oral glucose tolerance tests over several visits show that any given subject may exhibit large skin temperature variations between visits as well as over the course of a single visit of four hours' duration. These variations may result from several factors, including environmental and physiological conditions. It is necessary to understand the impact of large temperature variations on between sample stability. Monitoring skin temperature in a second pool of healthy individuals revealed that temperatures vary as much as 5° F. in the course of a typical workday. A study was conducted to generate two sets of data for each of three participants. The first data set contained noninvasive samples with large skin temperature excursions of up to approximately 8° F. between samples, while the second data set consisted of samples that were controlled within a 2° F. range.

Experimental Procedure

Three subjects, 2 males and 1 female, participated in the second study. Prior to measurement, the measurement site was occluded with a plug of RTV (room temperature vulcanizing) silicone rubber for forty-five minutes. A FOCSI 9 (fiber optic coupled scanning instrument) spectrometer instrument, manufactured by Instrumentation Metrics, Inc. of Tempe Ariz. was employed to collect all data. An optical coupling fluid, FLUORINERT FC-40, supplied by 3M Corporation, St. Paul Minn., was employed to enhance coupling between the measurement site and the fiber optic probe of the spectrometer. A reference scan (80% reflectance standard) and a polystyrene scan were collected with each sample. YSI temperature probes, supplied by YSI, Inc. of Yellow Springs Ohio were used to record skin temperature measurements near the spectral measurement site.

Five to eight samples were collected for both large and minimized skin temperature variation. Minimized skin temperature variation, herein referred to as controlled samples, was achieved by passively warming the measurement arm to approximately 91° F. with a small blanket. Uncontrolled samples, having large temperature variations, consisted of samples with skin temperatures varying from approximately 86° to 93° F.

Data Analysis

Preprocessing steps, including baseline correction, x-axis standardization, outlier detection, and conversion to absorbance were applied to the data set prior to analysis. Each sample, consisting of 16 raster scans was ensemble averaged. First derivative spectra were obtained using a thirty-five point first order Savitsky-Golay filter. The square of the standard deviation of each set of samples was calculated and is referred to as the spectral variance. The smaller the spectral variance, the simpler the matrix is for PLS (partial least squares) modeling.

In addition, RMSE (root mean square error) values were calculated to assess the sampling repeatability for controlled and uncontrolled samples. The entire usable wavelength regions for each detector (1100–1700 nm and 1400–2400 nm for the 1.9 μm and 2.6 μm detectors, respectively) were used to determine these values.

Results

Figure 8:
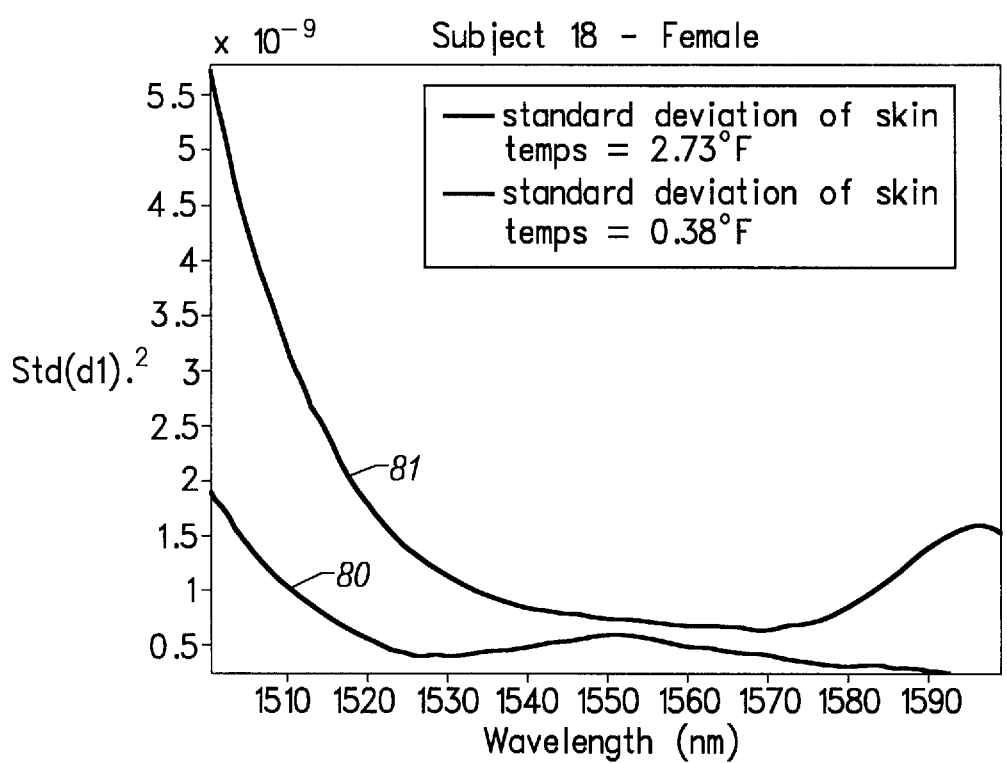
FIG. 8 presents a plot of spectral variance versus wavelength for a diabetic test subject, according to the invention.

FIG. 8 presents the spectral variance versus wavelength for clinic data for an exemplary subject from the first subject pool. The data includes samples from two separate clinic visits. Samples were separated according to skin temperature. The standard deviations of the skin temperatures were 0.38° F. (80) and 2.73° (81) F. When the skin temperature variations are small, spectral variance in the 1500–1600 nm spectral region is observed to be noticeably reduced.

Figure 9A:
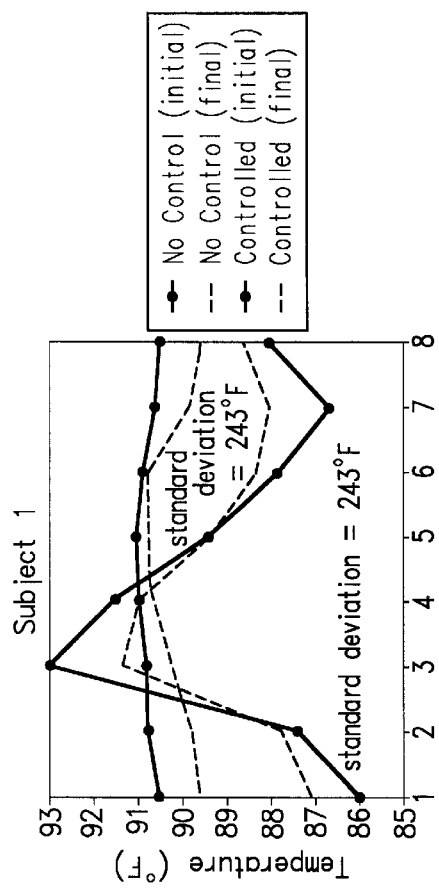
Figure 9B:
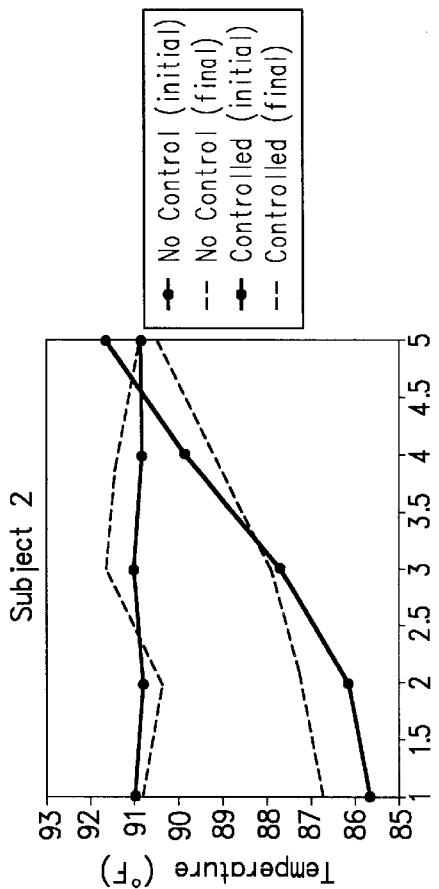
Figure 10A:
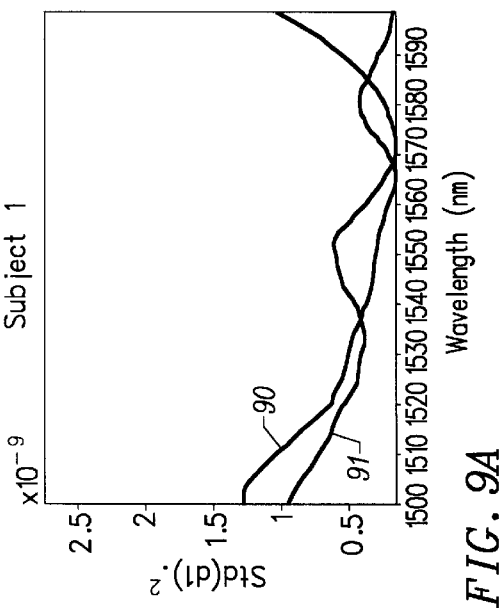
Figure 10B:
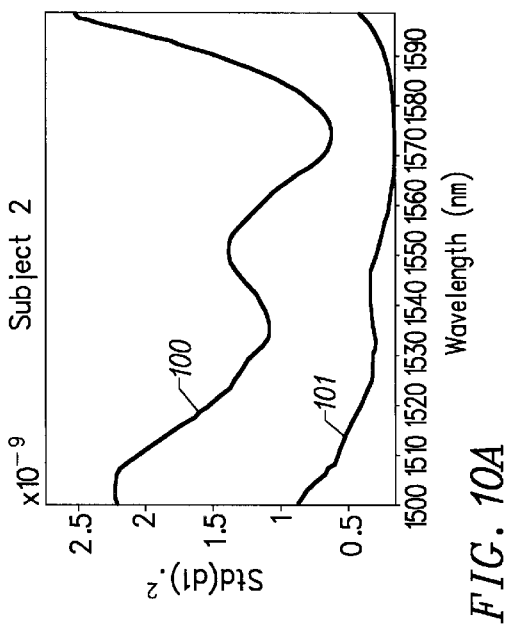
Figure 11B:
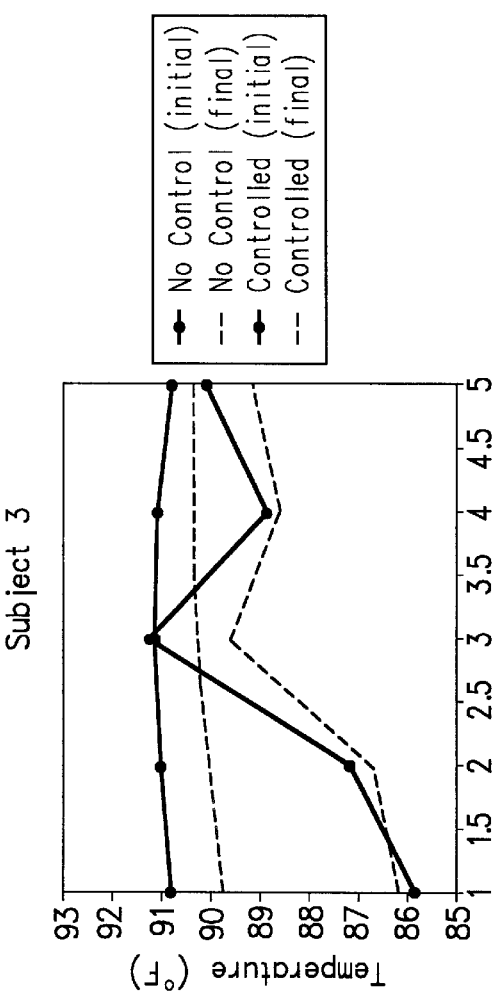
Figure 11A:
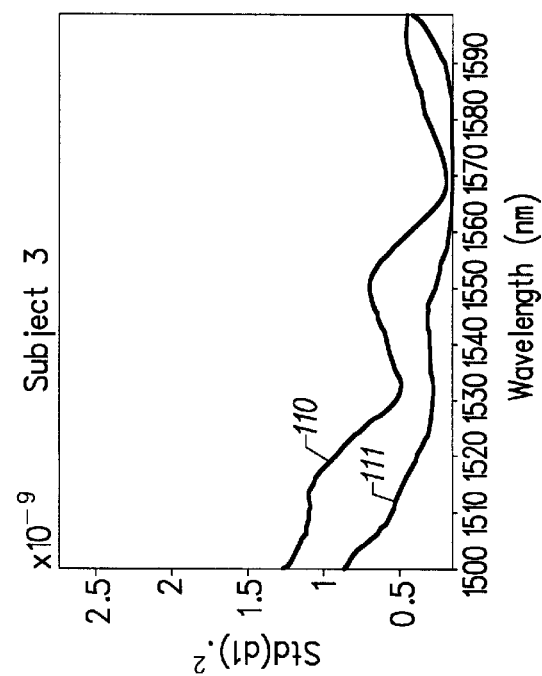
Figure 12:
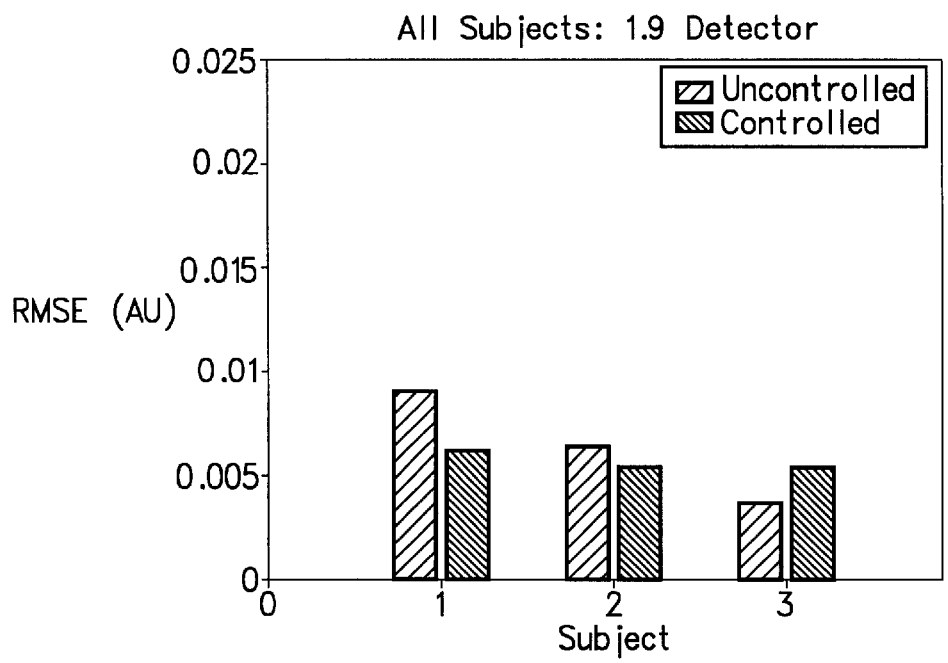
FIGS. 12 and 13 provide bar graphs of between sample variation relative to two different LED detectors for the three subjects of FIGS. 9–11, according to the invention.
Figure 13:

The study involving the second subject pool also indicates that minimization of skin temperature variation leads to reduced spectral variance. FIGS. 9–11 through present the spectral variance for the 1.9 μm detector versus wavelength for subjects 1 through 3. FIGS. 9a–11a provide plots of spectral variance for standard deviation of skin temperatures equal to 2.73° F. (90, 100, 110) and 0.38° F. (91, 101, 111) respectively, along with corresponding controlled and uncontrolled temperature profiles in FIGS. 9b–11b. Results are similar for the 1500–1600 nm region of the 2.6-μm detector. RMSE values are given in FIGS. 12 and 13, which indicate between sample repeatability of the data. Between-sample variation was moderately reduced on the 1.9-μm detector for subjects 1 and 2 and greatly reduced on the 2.6-μm detector for subjects 2 and 3 when temperature variation was controlled.

Both studies presented above suggest that samples with smaller variations in skin temperature result in reduced spectral variance in the wavelength region of interest.

In addition to skin temperature varying over time in a single individual, skin temperature ranges vary between individuals. For example, ambient temperature, time of day, physiological response to contact with the subject interface module of the instrument, the type of clothing and activity level all impact a person's skin temperature. Due to the large number of parameters involved, it is not feasible to define a single skin temperature at which noninvasive spectra should be collected. However, it is clear, that a method of minimizing skin temperature variation within a subject be reduces spectral variation within the wavelength region of interest. To minimize spectral variation, skin temperatures may be maintained at approximately 89–91° F. Wrapping the forearm with a blanket or other thermal wrapping is an effective method of raising the skin temperature prior to scanning and does not introduce large temperature transients during scanning. Another possible method of controlling skin temperature involves placing the arm on a temperature-controlled heat sink prior to scanning.

While the invention has been described herein with respect to control of skin temperature, the invention may also be applied to other tissue state parameters such as hydration or surface pH. Additionally, while the invention finds particular application in noninvasive blood glucose determination, the invention also is applicable to the measurement of other constituents of blood and tissue; for example, cholesterol, other lipids, BUN, and protein. Furthermore, the invention would be suitable for the detection of foreign substances in the blood such as ethanol and various other drugs and toxins.

Although the invention has been described herein with reference to certain preferred embodiments, one skilled in the art will readily appreciate that other applications may be substituted without departing from the spirit and scope of the present invention. Accordingly, the invention should only be limited by the claims included below.

What is claimed is:

1. A method for controlling spectral effects attributable to tissue state variations during NIR-based, non-invasive blood analyte determination, comprising the steps of:

determining a target range of values for a selected tissue state parameter, said tissue state parameter comprising skin temperature in the vicinity of a tissue measurement site on a body part of a live subject;

providing means for modifying said tissue state parameter;

providing a calibration model, developed using a calibration data set that includes spectral measurements on a group of exemplary subjects combined with associated skin temperature reference measurements, said calibration developed using multivariate analytical techniques, that correlates said spectral effects to variations in said tissue state parameter, said spectral effects comprising shifts in a peak water absorbance band in an NIP spectrum, wherein said model implicitly incorporates said shift information in multivariate regression coefficients;

monitoring said tissue state parameter by measuring an NIR spectrum and calculating values for said parameter from said spectrum according to said calibration model; and if said calculated value is outside of said target range, modifying said tissue state parameter until a measured value for said parameter is within said target range.

2. The method of claim 1, wherein said peak water absorbance band shifts to shorter wavelengths as skin temperature increases and wherein said peak water absorbance band shifts to longer wavelengths as skin temperature decreases;

wherein said shifts attenuate a net analyte signal.

3. The method of claim 2, wherein said peak water absorbance band occurs in a wavelength region at approximately 1450 nm.

4. The method of claim 2, wherein said step of determining a target range comprises:

empirically determining said target range by examining spectra from a calibration data set to determine a temperature range in which said shifts are minimized.

5. The method of claim 1, wherein said target range comprises a range of skin temperatures wherein said shifts are minimized, so that said attenuation of said net analyte signal is minimized.

6. The method of claim 5, wherein said target range is approximately eighty-nine to ninety one degrees, Fahrenheit.

7. The method of claim 1, wherein said means for modifying a tissue state parameter comprises one or both of:

means for actively controlling said skin temperature; and
   means for passively controlling said skin temperature.

8. The method of claim 7, wherein said active means and said passive means are employed in complementary fashion to maintain skin within said target range.

9. The method of claim 8, wherein said active means of control is employed to induce rapid changes in skin temperature.

10. The method of claim 7, wherein said passive means of control is employed for extended time periods.

11. The method of claim 7, wherein said means for passively controlling said skin temperature comprises a thermal wrap applied to said body part, wherein initial application of said thermal wrap causes a rise in skin temperature.

12. The method of claim 11, wherein skin temperature is maintained within said target range by one of loosening, tightening and removing said thermal wrap.

13. The method of claim 7, wherein said means for actively controlling said skin temperature comprises a temperature-controlled heat sink.

14. The method of claim 13, wherein said heat sink has a set point within said target range, and wherein said heat sink cools or warms said skin to maintain skin temperature within said target range.

15. The method of claim 13, wherein active control is localized to skin that comes into contact with said heat sink.

16. The method of claim 7, wherein said step of modifying said tissue state parameter comprises applying one or both of said means of control so that skin temperature is restored to said target range.

17. The method of claim 1, wherein said reference measurements span a range approximately equal to or greater than said target range.

18. The method of claim 1, wherein said reference measurements are made using a noninvasive temperature sensor placed in the immediate vicinity of the tissue measurement site.

19. The method of claim 1, wherein said step of monitoring said tissue state parameter comprises the steps of:

calculating an absorbance spectrum from said NIR spectrum;
   pre-processing said absorbance spectrum; and
   calculating a skin temperature value by applying said multivariate calibration model.

20. An apparatus for controlling spectral effects attributable to tissue state variations during NIR-based, non-invasive blood analyte determination, comprising:

means for modifying a selected tissue state parameter, wherein said tissue state parameter comprises skin temperature in the vicinity of a tissue measurement site on a body part of a live subject;

means for measuring an NIR spectrum at a tissue measurement site;

a calibration model that correlates said spectral effects to variations in said tissue state parameter, wherein said calibration model is developed using a calibration data set that includes spectral measurements or a group of exemplary subjects combined with associated skin temperature reference measurements, said spectral effects comprising shifts in a peak water absorbance band in an NIR spectrum;

means for monitoring said tissue state parameter by measuring an NIR spectrum and calculating values for said parameter from said spectrum according to said calibration model;

wherein said tissue state parameter is modified by said modifying means if said calculated value is outside of a target range until said parameter is within said target range.

21. The apparatus of claim 20, wherein said peak water absorbance band shifts to shorter wavelengths as skin temperature increases and wherein said peak water absorbance band shifts to longer wavelengths as skin temperature decreases;

wherein said shifts attenuate a net analyte signal.

22. The apparatus of claim 21, wherein said peak water absorbance band occurs in a wavelength region at approximately 1450 nm.

23. The apparatus of claim 21, wherein said target range comprises a range of skin temperatures wherein said shifts are minimized, so that said attenuation of said net analyte signal is minimized.

24. The apparatus of claim 21, wherein target range is empirically determined by examining spectra from a calibration data set to determine a temperature range in which said shifts are minimized.

25. The apparatus of claim 20, wherein said target range is approximately eighty-nine to ninety one degrees, Fahrenheit.

26. The apparatus of claim 20, wherein said means for modifying a tissue state parameter comprises one or both of:

means for actively controlling said skin temperature; and means for passively controlling said skin temperature.

27. The apparatus of claim 26, wherein said active means and said passive means are employed in complementary fashion to maintain skin within said target range.

28. The apparatus of claim 27, wherein said active means of control is employed to induce rapid changes in skin temperature.

29. The apparatus of claim 26, wherein said passive means of control is employed for extended time periods.

30. The apparatus of claim 26, wherein said means for passively controlling said skin temperature comprises a thermal wrap applied to said body part, wherein initial application of said thermal wrap causes a rise in skin temperature.

31. The apparatus of claim 30, wherein skin temperature is maintained within said target range by one of loosening, tightening and removing said thermal wrap.

32. The apparatus of claim 26, wherein said means for measuring an NIR spectrum comprises a NIR spectrometer instrument, wherein said spectrometer instrument includes a subject interface module.

33. The apparatus of claim 32, wherein said means for actively controlling said skin temperature comprises a temperature-controlled heat sink.

34. The apparatus of claim 33, wherein said heat sink has a set point within said target range, and wherein said heat sink cools or warms said skin to maintain skin temperature within said target range.

35. The apparatus of claim 33, wherein active control is localized to skin that comes into contact with said heat sink.

36. The apparatus of claim 32, wherein said heat sink is incorporated into said subject interface module, so that said heat sink is in contact with said tissue measurement site during use.

37. The apparatus of claim 26, wherein said tissue state parameter is modified by applying one or both of said means of control so that skin temperature is restored to said target range.

38. The apparatus of claim 20, wherein said reference measurements span a range approximately equal to or greater than said target range.

39. The apparatus of claim 20, wherein said reference measurements are made using a noninvasive temperature sensor placed in the immediate vicinity of the tissue measurement site.

40. The apparatus of claim 20, wherein said tissue state parameter is monitored by:

calculating an absorbance spectrum from said NIR spectrum;

pre-processing said absorbance spectrum; and calculating a skin temperature value by applying said multivariate calibration model.

41. A method for controlling spectral effects attributable to tissue state variations during NIR-based, non-invasive blood analyte determination, comprising the steps of:

determining a target range of values for a selected tissue state parameter, said tissue state parameter comprising skin temperature in the vicinity of a tissue measurement site on a body part of a live subject;

providing means for modifying said tissue state parameter;

providing a calibration model that correlates said spectral effects to variations in said tissue state parameter, said spectral effects comprising shifts in a peak water absorbance band in an NIR spectrum, said target range comprising a range of skin temperatures wherein said shifts are minimized;

monitoring said tissue state parameter by measuring an NIR spectrum and calculating values for said parameter from said spectrum according to said calibration model; and if said calculated value is outside of said target range, modifying said tissue state parameter until a measured value for said parameter is within said target range.

* * * * *

UNITED STATES PATENT AND TRADEMARK OFFICE
CERTIFICATE OF CORRECTION

PATENT NO. : 6,640,117 B2
DATED : October 28, 2003
INVENTOR(S) : Makarewicz et al.

It is certified that error appears in the above-identified patent and that said Letters Patent is hereby corrected as shown below:

<u>Title page,</u>
Item [74], *Attorney, Agent, or Firm:*, replace "Glenn Patent Group: Michael A. Glenn; Christopher Feil" with -- Glenn Patent Group; Michael A. Glenn; Christopher Pell --

Signed and Sealed this

Eighteenth Day of May, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,640,117 B2
DATED : October 28, 2003
INVENTOR(S) : Makarewicz et al.

It is certified that error appears in the above-identified patent and that said Letters Patent is hereby corrected as shown below:

<u>Title page,</u>
Item [74], *Attorney, Agent, or Firm*, replace "Glenn Patent Group; Michael A. Glenn; Christopher Pell" with -- Glenn Patent Group; Michael A. Glenn; Christopher Peil --

Signed and Sealed this

Fourteenth Day of December, 2004

JON W. DUDAS
*Director of the United States Patent and Trademark Office*